US010201456B2

(12) United States Patent
Pernot et al.

(10) Patent No.: US 10,201,456 B2
(45) Date of Patent: Feb. 12, 2019

(54) ABSORBENT CICATRIZATION DRESSING AND USES THEREOF FOR CHRONIC WOUNDS

(75) Inventors: Jean-Marc Pernot, Dijon (FR); Stephane Auguste, Varois et Chaignot (FR); Christelle Laurensou, Dijon (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 277 days.

(21) Appl. No.: 14/008,953

(22) PCT Filed: Mar. 29, 2012

(86) PCT No.: PCT/FR2012/050665
§ 371 (c)(1),
(2), (4) Date: Nov. 12, 2013

(87) PCT Pub. No.: WO2012/131263
PCT Pub. Date: Oct. 4, 2012

(65) Prior Publication Data
US 2014/0058310 A1 Feb. 27, 2014

(30) Foreign Application Priority Data
Mar. 31, 2011 (FR) ...................................... 11 52720

(51) Int. Cl.
*A61F 13/00* (2006.01)
*A61F 13/02* (2006.01)

(52) U.S. Cl.
CPC ........ *A61F 13/00042* (2013.01); *A61F 13/00* (2013.01); *A61F 13/00029* (2013.01); *A61F 2013/0091* (2013.01); *A61F 2013/00229* (2013.01); *A61F 2013/00251* (2013.01); *A61F 2013/00604* (2013.01); *A61F 2013/00676* (2013.01); *A61F 2013/00744* (2013.01); *A61F 2013/00748* (2013.01); *A61F 2013/00782* (2013.01)

(58) Field of Classification Search
CPC ................ A61F 13/00; A61F 13/00029; A61F 13/00042; A61F 2013/00229; A61F 2013/00251; A61F 2013/00604; A61F 2013/00676; A61F 2013/00744; A61F 2013/00748; A61F 2013/00782; A61F 2013/0091; A61F 13/0213; A61F 2013/00761; A61F 2013/00697; A61F 13/0246; A61F 2013/530306; A61F 2013/530613; A61F 2013/53024
See application file for complete search history.

(56) References Cited

U.S. PATENT DOCUMENTS

| 4,367,732 | A | * | 1/1983 | Poulsen | A61L 24/0094 |
| | | | | | 602/56 |
| 4,664,662 | A | * | 5/1987 | Webster | 602/47 |
| 4,913,943 | A | * | 4/1990 | Goossen | 428/36.1 |
| 5,393,599 | A | * | 2/1995 | Quantrille et al. | 442/57 |
| 5,948,529 | A | * | 9/1999 | Hastie | 428/373 |
| 6,171,594 | B1 | * | 1/2001 | Nielsen | A61L 15/40 |
| | | | | | 424/443 |
| 6,270,792 | B1 | * | 8/2001 | Guillemet et al. | 424/443 |
| 6,303,700 | B1 | * | 10/2001 | Chen | A61L 15/585 |
| | | | | | 424/448 |
| 2002/0037945 | A1 | * | 3/2002 | Nielsen | C09J 11/08 |
| | | | | | 523/111 |
| 2002/0038099 | A1 | * | 3/2002 | Griffiths | A61F 13/0203 |
| | | | | | 602/54 |
| 2003/0187115 | A1 | * | 10/2003 | Cinelli | A61F 13/02 |
| | | | | | 524/386 |
| 2004/0236260 | A1 | | 11/2004 | Griffiths et al. | |
| 2009/0137937 | A1 | * | 5/2009 | Truelsen | A61F 13/00008 |
| | | | | | 602/44 |
| 2009/0156974 | A1 | * | 6/2009 | Truelsen et al. | 602/45 |
| 2010/0168633 | A1 | * | 7/2010 | Bougherara | A61F 13/0283 |
| | | | | | 602/43 |

(Continued)

FOREIGN PATENT DOCUMENTS

GB 2401879 11/2004
WO WO 02/03898 1/2002

(Continued)

OTHER PUBLICATIONS

WO2008/149036; the English equivalent is PGPub 20100285129.*
Jagisch et al.: "16. Styrenic Block Copolymers"; Handbook of Pressure-Sensitive Adhesive Technology by Donatas Satas (Editor), $3^{rd}$ Edition, pp. 346-398 (1999).
Brown et al.: "Fibroblast Migration in Fibrin Gel Matrices"; American Journal of Pathology, vol. 142, No. 1, pp. 273-283, Jan. 1993.

*Primary Examiner* — Peter S Vasat
(74) *Attorney, Agent, or Firm* — Hamre, Schumann, Mueller & Larson, P.C.

(57) ABSTRACT

One subject of the present invention is a dressing essentially consisting of:
an absorbent nonwoven compress formed from a mixture:
of bicomponent thermal bonding non-absorbent fibers, of core-shell type, said core being made of polyester (polyethylene terephthalate, PET) and the shell being made of polyethylene;
of bicomponent superabsorbent fibers of core-shell type with a core made of polyacrylonitrile and a shell made of polyacrylate;
and
a net fabric made from a hydrocolloid elastomer mass partially covering the face of the compress intended to come into contact with the wound.
This product is especially intended to promote the healing of chronic wounds by optimizing the debridement.

30 Claims, No Drawings

(56) References Cited

U.S. PATENT DOCUMENTS

2010/0285129 A1* 11/2010 Laurensou ............ A61K 31/505
424/484

FOREIGN PATENT DOCUMENTS

| WO | WO 2007/025544 | 3/2007 |
| WO | WO 2007/025546 | 3/2007 |

* cited by examiner

ABSORBENT CICATRIZATION DRESSING AND USES THEREOF FOR CHRONIC WOUNDS

The present invention relates to a dressing comprising an absorbent nonwoven compress and an elastomer contact layer comprising hydrocolloids. This dressing is very effective in the care of wounds for which it is desired to promote healing. It makes it possible to manage the exudates generated by the wound and also the presence of fibrin, without it being necessary to resort to complementary debridement means such as surgery or enzymes.

The natural healing of a wound takes place in three successive phases, each of these phases being characterized by specific cellular activities: the debridement phase, the proliferation (or granulation) phase and the epithelialization phase. Throughout the healing process, the wound produces fluid or viscous exudates which must be absorbed by the dressing.

The natural debridement capacities of the wound may be insufficient when the trauma is significant or when the patient suffers from similar pathologies, such as venous pathologies or diabetes. In these cases, a considerable lengthening of the duration of the debridement phase is observed resulting in chronic wounds that are difficult to care for, such as for example leg ulcers.

In the case of wounds for which the natural debridement process is insufficient, it is necessary to remove the fibrinous tissue without disturbing the proliferation phase. The removal of this fibrinous tissue is commonly denoted by the term "assisted debridement" as opposed to natural debridement.

Depending on the technique used, assisted debridement may be described as mechanical or surgical debridement, enzymatic debridement, autolytic debridement or biological debridement.

Surgical or mechanical debridement is a rapid technique which consists in cutting out the fibrinous tissue, either using a bistoury, tweezers, scissors or a Brock curette, or using sophisticated apparatus via jets of pressurized water or laser excision. This technique is carried out in the patient's bed or in a surgical environment depending on the gravity of the wound.

However, this technique is often painful and may lead to bleeding and sometimes even a hemorrhage. It is then traumatic for the patient. It also commonly requires analgesic medication beforehand which lengthens the duration of the care.

Autolytic debridement consists in depositing absorbent dressings based on particular gelling fibers on the wound.

The dressings used for the debridement are generally needle-punched nonwovens of gelling fibers of alginate or of carboxymethyl cellulose (a product of this type is sold under the reference Aquacel® for example).

These dressings have the drawback of lacking cohesion and of disintegrating as the exudates are absorbed, so much so that they leave debris in the wound and it is impossible to remove them in a single piece. In order to solve this problem, it has been proposed to deposit a perforated adhesive layer on the surface of the nonwoven, so as to retain the fibers that are detached from the nonwoven while guaranteeing the passage of the exudates (WO 2002/03898). The proposed diameter of the perforations is of the order of 5 to 8 mm.

It has also been proposed, in document WO 2007/025546, to use a nonwoven of superabsorbent fibers, in which the fibers are needle punched so as to space them out sufficiently so that, once swollen, they continue to allow the exudates to pass through. By spacing out the fibers, the cohesion of the nonwoven reduces so much so that it becomes necessary to prevent the fibers which would be detached from the nonwoven from polluting the wound. Application WO 2007/025544 thus makes provision to deposit, by fiberization, yarns of thermoplastic material on the nonwoven by forming loops, the points of intersection of which are welded. The basis weight of the yarns must be less than 100 g/m2 in order to ensure the rapid initial absorption of the exudates by the absorbent layer. Specifically, it is imperative not to reduce the absorption rate and capacity of the nonwoven by inserting an intermediate layer between the wound and the nonwoven. Similarly, this intermediate layer must not adversely affect the autolytic debridement capacity of these dressings.

These dressings are a long way from enabling optimal debridement. Their use is often combined with mechanical debridement which requires the patient to go through traumatic and painful actions. It would therefore be useful to reduce or eliminate recourse to this mechanical debridement.

It would thus be desirable to have a dressing for the care of wounds, in particular chronic wounds, which—despite the presence of an intermediate layer between the wound and the nonwoven—does not adversely effect the amount and rate of absorption of the exudates and the autolytic debridement capacities of the dressing and which preferably enables an optimized removal of the fibrin in order to reduce or eliminate recourse to surgical actions. This dressing should also make it possible to promote the healing of the regions of the wound that are free of fibrin and do not adversely effect, during its removal, the reconstruction of the tissues. Finally, this dressing should be cohesive and should not cause pain during its removal.

The applicant has developed a dressing that complies with these desires, which dressing comprises a superabsorbent nonwoven which is covered, on the portion opposite the wound, with a particular contact layer. This layer makes it possible to guarantee the painless removal of the used dressing while ensuring the removal of the fibrin. Against all expectations, the interposition of this particular layer between the wound and the nonwoven compress has not reduced the capacity of the dressing to absorb the exudates and its autolytic debridement capacity. The applicant has additionally observed that the fibrin may stick to the dressing and may be removed in blocks when the dressing is taken off.

The present invention thus makes it possible to optimize the healing of wounds, in particular of chronic wounds, by providing, for the first time, a dressing that simultaneously promotes autolytic debridement and granulation of the wound and makes it possible to take care of all the portions of the wound, which are not necessarily at the same healing stage.

The dressing of the invention furthermore makes it possible to absorb liquid exudates very rapidly while maintaining a moist environment at the wound. The exudates are absorbed by the nonwoven compress, whilst the contact layer gels in contact with the exudates.

The moist environment created at the surface of the wound makes it possible to promote healing.

Finally, the dressing of the invention is cohesive and does not tear when it is removed.

In the dressing structures of the invention comprising the assembly of a nonwoven of superabsorbent fibers and a layer intended to come into contact with the wound, it is advisable to guarantee a rapid and constant absorption over time of the exudates and to avoid maceration of the wound and of the perilesional skin.

The objective of the present invention is to provide a cohesive dressing, consisting of a particular nonwoven and of a specific contact layer, which enables the painless removal of the dressing while ensuring the rapid absorption of exudates without adversely affecting the autolytic debridement capacity of the dressing, and preferably while promoting the removal of fibrin in blocks, and to preserve the integrity of the proliferative tissues and promote the growth thereof, and finally to guarantee a rapid and constant absorption of the exudates throughout the use thereof in order to prevent problems of maceration.

The specific contact layer consists of an elastomer composition in order to remain flexible and adopt the shape of the body.

The dressings of the invention are painless to remove, and their action on the healing of the regions without fibrin is beneficial since the contact layer, by gelling, does not adhere to the wound and creates a favorable moist environment. The absorption of the fibrin and of the exudates by the nonwoven is retained while avoiding the reduction in the size of the openings of the contact layer during the absorption of the exudates.

Thus, the subject of the present invention is a dressing comprising:

a—an absorbent nonwoven compress formed from a mixture of superabsorbent, preferably bicomponent, fibers and of thermal bonding non-absorbent fibers, all of the fibers being thermally bonded, and, b—a contact layer that partially covers the face of the compress intended to come into contact with the wound, said layer comprising openings that allow the passage of exudates from the wound and having a basis weight that ranges from 110 to 500 g/m2, and said layer being formed from a composition comprising an elastomeric matrix and hydrocolloids, the proportion of hydrocolloids being between 2% and 20% by weight of the weight of said composition.

According to one preferred embodiment of the invention, the dressing comprises:

a—an absorbent nonwoven compress formed from a mixture of bicomponent superabsorbent fibers of core-shell type with a core made of polyacrylonitrile and a shell made of polyacrylate and of bicomponent thermal bonding non-absorbent fibers of core-shell type, said core being made of polyester (polyethylene terephthalate PET) and a shell being made of polyethylene, all of the fibers being thermally bonded, and, b—a contact layer that partially covers the face of the compress intended to come into contact with the wound, said layer comprising openings that allow the passage of exudates and having a basis weight that ranges from 150 to 200 g/m2, said layer being formed from a composition comprising an elastomeric matrix and hydrocolloids, the hydrocolloids representing from 2% to 20% by weight of the total weight of said composition, and said layer covering, before being exposed to the exudates of the wound, between 55% and 65% of the face of the compress which is opposite the wound.

The dressing in accordance with the present invention comprises an absorbent layer formed from a nonwoven obtained from a mixture of superabsorbent fibers and of non-absorbent fibers.

The expression "superabsorbent" is understood to denote here fibers that have a very high capacity for absorbing liquids, preferably greater than or equal to 10 g of water (or of saline solution such as physiological serum) per gram, more preferably greater than 20 g of water per gram, and more preferably greater than 30 g of water per gram.

According to the invention, the superabsorbent fibers preferably consist of two different materials. These materials may be distributed in a side-by-side configuration, or preferably in a core-shell configuration.

The first material intended to form an outer part of the fiber, preferably the shell, must be capable of forming a gel with the exudates of the wound and will advantageously be formed from one or more crosslinked and/or partially crosslinked polymers, such as in particular polymers of acrylic acid and/or polymers of acrylic acid salts, especially sodium or ammonium acrylate.

The second component that will preferably form the core of the superabsorbent fibers will preferably be non-gelling and compatible with the first material in order to guarantee the stability of the fiber after formation of a gel by the first material. It may be formed from any type of polymer that is stable in an aqueous medium and compatible with the material of the shell in order to result in a stable bicomponent fiber.

Advantageously, this second material is formed from polyacrylonitrile.

The superabsorbent fibers advantageously have a size between 2 and 6 dtex.

Superabsorbent fibers that can be used within the context of the invention are, for example, sold by the company TOYOBO CO. LTD. under the name LANSEAL® F.

Non-absorbent fibers are thermal bonding fibers capable of reinforcing and stabilizing the three-dimensional structure of the nonwoven by forming a reinforcement which results from the bonding of these fibers with one another and/or of these fibers with the superabsorbent fibers.

These second fibers may consist of a single thermoplastic material such as, for example, a polyethylene, a polypropylene or a polyester of low melting point.

Advantageously, these second fibers will also consist of two different materials distributed in a side-by-side or preferably core-shell configuration.

The length of these fibers may be of the order of 10 to 100 mm, preferably of 25 to 75 mm.

Within the context of the present invention, bicomponent thermal bonding non-absorbent fibers of core-shell type in which the core is formed from a polyester such as in particular polyethylene terephthalate, and the shell is formed of polyethylene, are particularly preferred.

Generally, the nonwoven that forms the absorbent compress of the dressings according to the invention will be obtained from mixtures that incorporate more than 50% by weight, preferably more than 60% by weight, of superabsorbent fibers.

The weight ratio between the absorbent fibers and the thermal bonding non-absorbent fibers may be between 20/80 and 80/20, preferably between 60/40 and 80/20.

Excellent results have been obtained using a mixture comprising 30% by weight of non-absorbent fibers and 70% by weight of superabsorbent fibers.

This nonwoven is generally obtained by thermal bonding, or by needle punching and thermal bonding of the mixture of fibers.

The needle punching operation makes it possible in particular to orientate the superabsorbent fibers in a substantially vertical direction relative to the plane of the nonwoven. This orientation of the fibers makes it possible to reduce the transverse propagation of exudates absorbed by the dressing containing this nonwoven and therefore makes it possible to reduce the risks of maceration and consequently of deterioration of the perilesional skin.

The thermal bonding operation makes it possible to improve the tear resistance of the nonwoven after absorption, by creating anchoring points between the fibers of the nonwoven. It is necessary to reinforce the cohesion of the nonwoven in order to enable the removal of the used dressing without tearing it.

The assembling of the fibers will be carried out under conditions that make it possible to obtain a nonwoven having a thickness between 0.6 and 3 mm, preferably of 2 mm, and a basis weight between 40 and 400 g/m2, preferably of the order of 185 g/m2.

The nonwoven compress may be manufactured according to the process described in document GB 2 401 879.

Various active substances can be incorporated into the nonwoven, such as for example substances with an antimicrobial activity, in particular silver salts such as for example silver sulfate, silver chloride, silver nitrate, silver sulfadiazine, quaternary ammoniums, polyhexamethylene biguanide and chlorhexidine. It is possible to incorporate other substances that promote healing such as, for example, growth factors or polysulfated oligosaccharides such as the sucrose octasulfate potassium salt.

It is also possible to incorporate fibers endowed with antibacterial properties into the nonwoven. For example, these fibers could incorporate a metal (silver, copper, zinc) or another antibacterial active agent. In the case of a metal, these fibers may be obtained in various ways: by incorporation of the metal into the polymer matrix during extrusion (PP, PET, PA) or by application of the metal in the spin finish during the spinning process (acrylic, viscose). The metal used for manufacturing these fibers may be in the form of salts, zeolites, ceramics or nanoparticles.

The elastomer composition containing hydrocolloids that is capable of being used for the manufacture of the dressings in accordance with the invention comprises an elastomeric matrix in which hydrocolloids are preferably dispersed homogeneously.

The contact layer of the dressing of the invention advantageously makes it possible not to adhere to the wound and prevents any pain on removal of the dressing.

By maintaining a moist medium at the surface of the wound while avoiding contact with the exudate-loaded absorbent compress, it improves healing. The incorporation of hydrocolloids gives the elastomer composition a hydrophilic nature and promotes the vectorization of active agents capable of promoting the treatment of the wound.

Said composition comprises one or more elastomers chosen from poly(styrene-olefin-styrene) block polymers. The block copolymers used within the context of the invention are advantageously triblock copolymers of ABA type comprising two styrene thermoplastic end blocks A and an elastomer central block B which is an olefin, optionally combined with diblock copolymers of AB type comprising a styrene thermoplastic block A and an elastomer block B which is an olefin. The olefin blocks B of these copolymers may consist of unsaturated olefins such as for example isoprene or butadiene or of saturated olefins such as for example ethylene-butylene or ethylene-propylene.

In the case of a mixture of triblock copolymers ABA and of diblock copolymers AB, it will be possible to use commercial mixtures of triblock copolymers ABA and of diblock copolymers AB that are already available or to produce mixtures of any proportion previously chosen from the two independently available products.

The triblock copolymers with an unsaturated central block are well known to a person skilled in the art and are in particular sold by the company Kraton Polymers under the name KRATON® D.

As examples of poly(styrene-isoprene-styrene) (abbreviated to SIS) copolymers, mention may thus be made of the products sold under the names KRATON® D1107 or KRATON® D1119 BT or else the products sold by the company Exxon Mobil Chemical under the name VECTOR® such as for example the products sold under the name VECTOR® 4113. An example of polystyrene-butadiene-styrene) copolymers is the product sold under the name KRATON® D1102.

As examples of commercial mixtures of triblock copolymers ABA and of diblock copolymers AB in which B is isoprene, mention may be made of the products sold by the company Exxon Mobil Chemical under the name VECTOR® 4114.

All these copolymers based on isoprene or on butadiene generally have a styrene content of between 10% and 52% by weight relative to the total weight of said copolymer.

Within the context of the present invention, use will preferably be made of the poly(styrene-isoprene-styrene) (abbreviated to SIS) triblock block copolymers having a styrene content of between 14% and 52% and preferably of between 14% and 30% by weight relative to the weight of said poly(SIS).

Preferably, for producing the compositions of the present invention, use will be made of triblock block copolymers and in particular the product sold by the company Kraton Polymers under the name KRATON® D1119 BT.

The triblock copolymers having a saturated central block are also well known to a person skilled in the art and are, for example, sold:

by the company Kraton Polymers under the name KRATON® G, and in particular under the name KRATON® G1651, KRATON® G1654 or KRATON® G1652 for poly(styrene-ethylene-butylene-styrene) (abbreviated to SEBS) block copolymers;

by the company Kuraray under the name SEPTON® for poly(styrene-ethylene-propylene-styrene) (abbreviated to SEPS) block copolymers.

As an example of commercial mixtures of triblock and diblock copolymers, mention may be made of the product sold by the company Kraton Polymers under the name KRATON® G1657, the olefin block of which is ethylene-butylene.

As an example of a particular mixture of triblock and diblock copolymers that can be produced within the context of the present invention, mention may be made of the mixture:

of a triblock SEBS, such as in particular the product sold by the company Kraton Polymers under the name KRATON® G1651; and of a poly(styrene-olefin) diblock copolymer such as in particular the poly(styrene-ethylene-propylene) sold by the company Kraton Polymers under the name KRATON® G1702.

Within the context of the present invention, SEBS or SEPS triblock copolymers having a styrene content of between 25% and 45% by weight relative to the weight of said SEBS or SEPS will be preferred. Preferably, use will be made of triblock block copolymers and in particular the products sold by the company Kraton Polymers under the names KRATON® G1651 and KRATON® G1654.

Generally, the elastomer will be used in suitable amounts depending on the saturated or unsaturated nature of the olefin central block of the block copolymer. Thus, in the case of a triblock copolymer having an unsaturated central block it will be used in an amount of the order of 10% to 30% by weight, preferably of 10% to 20% by weight, relative to the total weight of the composition. In the case of a triblock copolymer having a saturated central block, it will be used in an amount of the order of 3% to 10% by weight, preferably of 4% to 7% by weight, relative to the total weight of the composition.

The expression "hydrocolloid" or "hydrocolloid particles" is understood to denote here any compound customarily used by a person skilled in the art for its ability to absorb aqueous liquid such as water, physiological serum or the exudates of a wound.

As suitable hydrocolloids, mention may for example be made of pectin, alginates, natural vegetable gums such as in particular Karaya gum, cellulose derivatives such as carboxymethyl celluloses and the alkali metal salts thereof such as sodium or calcium salts thereof, and also synthetic polymers based on acrylic acid salts, known under the name "superabsorbents", such as for example the products sold by the company BASF under the name LUQUASORB® 1003 or by the company Ciba Specialty Chemicals under the name SALCARE® SC91 and also mixtures of these compounds.

Some of these superabsorbents described as "microcolloids" since they have a particle size of less than 10 micrometers can of course be used within the context of the production of the composition.

The hydrocolloids that are preferred within the context of the present invention are the alkali metal salts of carboxymethyl cellulose, and in particular sodium carboxymethyl cellulose (CMC). The size of the hydrocolloid particles is for example between 50 and 100 microns, in particular of the order of 80 microns.

The amount of hydrocolloids incorporated into the elastomer composition will advantageously be of the order of 2% to 20% by weight, preferably of 5% to 18% by weight, more preferably of 8% to 18% by weight, more preferably of 12% to 16% by weight, relative to the total weight of the elastomer composition.

Hydrocolloids, introduced in too large an amount into a perforated contact layer, reduce the absorption capacity of a nonwoven based on superabsorbent fibers as the gel forms. Indeed, the high absorption capacity of the hydrocolloids leads to a swelling of the contact layer, so much so that the holes of the mesh may become blocked. The absorbent nonwoven no longer directly absorbs the exudates but absorbs the exudates present in the hydrocolloid absorbent layer which reduces the absorption capacity of the dressing and creates problems of maceration.

Said composition comprises one or more elastomers chosen from poly(styrene-olefin-styrene) block polymers in combination with one or more plasticizing compounds and, if necessary, one or more antioxidants.

The elastomer compositions of the dressings according to the present invention comprise one (or more) plasticizing compound(s) intended to improve their stretching, flexibility, extrudability or processing properties.

They will preferably be liquid compounds, compatible with the olefin central block of the block copolymers used.

Among the plasticizing compounds capable of being used for this purpose, mention may in particular be made of plasticizing mineral oils, irrespective of the nature of the central block. Mention may also be made of polybutenes—such as for example the products sold by the company BP Chemicals under the name NAPVIS® 10—or else of phthalate derivatives such as dioctyl phthalate or dioctyladipate, when the central block is unsaturated.

Alternatively, it is also possible to use synthetic products based on liquid mixtures of saturated hydrocarbons such as for example the products sold by the company Total under the name GEMSEAL® and in particular the product GEMSEAL® 60 which is an isoparaffinic mixture derived from a completely hydrogenated petroleum cut. Use will preferably be made of these products with a triblock copolymer comprising a saturated central block.

Within the context of the present invention, use will preferably be made of plasticizing oils and in particular of mineral oils formed from compounds of paraffinic, naphthenic or aromatic nature or mixtures thereof in variable proportions.

Among the plasticizing oils that are particularly suitable, mention may be made of:
 the products sold by the company Shell under the names ONDINA® and RISELLA® which consist of mixtures based on naphthenic and paraffinic compounds;
 the products sold under the name CATENEX® which consist of mixtures based on naphthenic, aromatic and paraffinic compounds.

Particularly preferably, use will be made of a mineral plasticizing oil chosen from the products sold under the names ONDINA® 963 and ONDINA® 919.

These plasticizing compounds may be used in an amount of the order of 20% to 65% by weight, preferably of 30% to 50% by weight, relative to the total weight of the hydrocolloid elastomer composition.

According to one embodiment, these compositions are adherent: they have the property of adhering to the skin without adhering to the wound. They comprise one or more compounds referred to as "tackifiers" such as those customarily used by a person skilled in the art in the preparation of elastomer-based pressure-sensitive adhesives. For a detailed description of these products, reference may be made to the work by Donatas Satas "Handbook of Pressure Sensitive Technology", 3rd Edition, 1999, pages 346 to 398.

Within the context of the present invention, the use of a contact layer which has a low adherent strength will be preferred. This is because this low adherent strength enables the nursing staff to have both their hands available once the dressing is applied, in order to apply a secondary element such as for example support bandages, or even to reposition the dressing without impairing the healthy tissues. Such dressings are described as micro-adherent.

Generally, it will be possible to use one (or more) tackifying product(s) which will be incorporated into the elastomeric matrix in a proportion of the order of 1% to 50% by weight, relative to the total weight of the hydrocolloid elastomer composition, which will be determined as a function of the nature and of the relative proportion of the other constituents of the latter, in order to achieve the desired micro-adherent strength for the dressing.

Preferably, the tackifying product(s) will represent from 10% to 45% by weight, and more preferably from 15% to 40% by weight of the total weight of the hydrocolloid elastomer composition.

The tackifying products capable of being used within the context of the present invention will be able to be chosen from tackifying resins, low molecular weight polyisobutylenes or mixtures thereof.

Among the tackifying resins capable of being used according to the invention, mention may be made of modified terpene or polyterpene resins, rosin resins, hydrocarbon resins, mixtures of cyclic, aromatic and aliphatic resins, or mixtures of these resins.

Such products are sold, for example:
by the company Arakawa Chemical Industries under the name ARKON® P which are hydrogenated polycyclopentadiene resins;
by the company Exxon Chemical under the name ESCOREZ® and in particular the 5000 series of resins which are hydrogenated;
by the company Goodyear under the name WINGTACK®, and in particular WINGTACK® 86 which is a synthetic resin formed from C5/C9 copolymers or WINGTACK® 10 which is a resin based on synthetic polyterpene;
by the company Hercules under the name KRISTALEX® and in particular KRISTALEX® 3085 which is a resin based on α-methylstyrene.

Generally, in order to prevent coloring and stability problems of unsaturated resins, the use of hydrogenated resins, in particular with triblock copolymers having a saturated central block, is preferred since they are much more compatible with the latter than in WINGTACK type unsaturated resins that are essentially used with triblock copolymers having an unsaturated central block.

Among the latter, use will preferably be made of ESCOREZ® resins of the 5000 series and very particularly the ESCOREZ® 5380 resin.

The tackifying resins may be used alone or as a mixture with other tackifying products, preferably in a proportion of 10% to 50% by weight, and more particularly of 15% to 40% by weight, relative to the total weight of the composition.

Among the low molecular weight polyisobutylenes capable of being used as tackifying products, mention may be made of the polyisobutylenes having a molecular weight of the order of 40000 to 80000 daltons, such as for example the products sold by the company BASF under the name OPPANOL® and in particular the products sold under the names OPPANOL® B12 and OPPANOL® B15 or by the company Exxon Chemical under the name Vistanex and in particular the LM-MH grade.

These polyisobutylenes will be able to be used alone or as a mixture with other tackifiers in combination with triblock copolymers having an unsaturated central block. Their proportion will be able to vary, in this case, from 5% to 30% by weight, and more particularly from 8% to 15% by weight, relative to the total weight of the composition.

The compositions capable of being used for the manufacture of dressings in accordance with the invention may additionally comprise one or more antioxidants.

The expression "antioxidants" is understood to denote here the compounds commonly used by a person skilled in the art for ensuring the stability of the compounds that are incorporated into the formulation of adhesive masses, in particular the tackifying resins and the block copolymers, with respect to oxygen, heat, ozone and ultraviolet radiation.

As examples of suitable antioxidants, mention may be made of:
phenolic antioxidants, such as in particular the products sold by the company Ciba Specialty Chemicals under the names IRGANOX® 1010, IRGANOX® 565 and IRGANOX® 1076;
sulfur-containing antioxidants, such as in particular zinc dibutyldithiocarbamate sold by the company AKZO under the name PERKACIT® ZDBC.

These antioxidants will be able to be used in an amount of the order of 0.05% to 1% by weight, preferably from 0.1% to 0.5% by weight, relative to the total weight of the elastomer composition.

Within the context of the present invention, the use of IRGANOX® products, and in particular of the product IRGANOX® 1010, will be preferred.

Various compounds may additionally be added to the formulation of the elastomer compositions, such as in particular adjuvants or active agents commonly used in the field of wound treatment or in the pharmacological field.

The composition may contain active principles that have a favorable role in wound treatment. These active principles may especially induce or accelerate healing by acting during the debridement and/or granulation phase of the wound. It has been possible to observe that the contact layer of the invention is a very good vector for the release of the active principle(s), especially owing to the presence of hydrocolloids.

These active agents will be able to be used in an amount of the order of 0.01% to 20% by weight, preferably from 1% to 15% by weight and in particular from 2% to 10% by weight relative to the total weight of the composition.

Among the active substances capable of being used within the context of the invention, mention may be made, by way of example, of bactericidal or bacteriostatic agents, agents that promote healing, painkillers or anti-inflammatories.

As adjuvants, mention may thus be made of dyestuffs, fillers, odor absorbers or trappers, UV screening agents, pH regulators, microcapsules or microspheres that may optionally contain active agents, vaseline to give the dressing an oily appearance or polymers or surfactants to optimize the gelling rate, wettability or release of the active agents of the composition.

When the composition contains unsaturated polymers, use may thus be made of the copolymer AcResin® in order to increase gelling; it is also possible to use the surfactant MONTANOX® 80 or the polymer SEPINOV® EMT 10 both sold by the company SEPPIC to optimize the gelling rate, the wettability or the release of active agents optionally present in the composition.

Within the context of the production of dressings which use a composition based on elastomer copolymers having a saturated central block, use will preferably be made of compositions which, for a total of 100% by weight, comprise:
0.05% to 1% by weight of antioxidant;
10% to 50% by weight of tackifying resin;
2% to 20%, preferably from 12% to 16%, by weight of hydrocolloid, and in particular of sodium carboxymethyl cellulose;
20% to 65% by weight of plasticizer, and in particular of a plasticizing mineral oil;
3% to 10% by weight of a poly(styrene-ethylene-butylene-styrene) or polystyrene-ethylene-propylene-styrene) triblock polymer;
1% to 15% by weight of a copolymer consisting of a salt of 2-methyl-2-[(1-oxo-2-propenyl)amino]-1-propanesulfonic acid and of the 2-hydroxyethylester of propenoic acid.

Within the context of the production of dressings which use a composition based on elastomer copolymers having a saturated central block, use will preferably be made of compositions which, for a total of 100% by weight, comprise:
0.05% to 1% by weight of antioxidant;
10% to 50% by weight of tackifying resin;

2% to 20%, preferably from 12% to 16%, by weight of hydrocolloid, and in particular of sodium carboxymethyl cellulose;

20% to 65% by weight of plasticizer, and in particular of a mineral oil;

3% to 10% by weight of a poly(styrene-ethylene-butylene-styrene) or polystyrene-ethylene-propylene-styrene) triblock polymer.

Another composition based on elastomer copolymers having a saturated central block could comprise, for a total of 100% by weight:

0.05% to 1% by weight of antioxidant;

2% to 20%, preferably from 12% to 16%, by weight of hydrocolloid, and in particular of sodium carboxymethyl cellulose;

20% to 65% by weight of plasticizer, and in particular of a mineral oil;

3% to 25% by weight of a poly(styrene-ethylene-butylene-styrene) or polystyrene-ethylene-propylene-styrene) triblock polymer.

Within the context of the production of dressings which use a composition based on elastomer copolymers having an unsaturated central block, use will preferably be made of compositions which, for a total of 100% by weight, comprise:

0.05% to 1% by weight of antioxidant;

10% to 60% by weight of tackifying resin;

2% to 20%, preferably from 12% to 16%, by weight of hydrocolloid, and in particular of sodium carboxymethyl cellulose;

10% to 65% by weight of plasticizer, and in particular of a mineral oil or of a phthalate derivative;

5% to 25% by weight of a polystyrene-butadiene-styrene) or poly(styrene-isoprene-styrene) triblock polymer;

1% to 15% by weight of a copolymer consisting of a salt of 2-methyl-2-[(1-oxo-2-propenyl)amino]-1-propanesulfonic acid and of the 2-hydroxyethylester of propenoic acid.

One particularly preferred composition comprises, for a total of 100% by weight:

0.05% to 1% by weight of antioxidant;

30% to 40% by weight of tackifying resin;

2% to 20%, preferably from 12% to 16%, by weight of hydrocolloid, and in particular of sodium carboxymethyl cellulose;

35% to 45% by weight of plasticizer, and in particular of a plasticizing mineral oil;

4% to 6% by weight of a poly(styrene-ethylene-butylene-styrene) or poly(styrene-ethylene-propylene-styrene) triblock polymer;

2% to 8% by weight of a copolymer consisting of a salt of 2-methyl-2-[(1-oxo-2-propenyl)amino]-1-propanesulfonic acid and of the 2-hydroxyethylester of propenoic acid.

The compositions defined above can be manufactured according to a hot-melt process well known to a person skilled in the art, by hot-blending of the various constituents at a temperature between 90° C. and 160° C. and preferably between 110° C. and 140° C. It is preferred to deposit the hydrocolloid elastomer composition by dip coating an etched cylinder in the previously hot-blended composition. The composition thus molded is then transferred by the cylinder to the nonwoven.

Practically, the elastomer composition will be protected by covering it, at least on its face intended to come into contact with the wound, with a protective layer or film, which will be able to be removed by peeling before use of the dressing.

The contact layer comprising the elastomer composition described above may take various forms, such as a perforated sheet of elastomer composition, a net fabric of extruded or molded composition, or a knit coated with said elastomer composition. In order to obtain the required adhesion, a flat contact layer will be preferred.

The size of the openings of the contact layer is preferably chosen so that their mean diameter or their mean length is between 1 and 3 mm, preferably between 1 and 2 mm, in particular of the order of 1.5 mm. The surface area of the openings is, for example, between 0.5 and 10 mm2, preferably between 0.8 and 6 mm2.

According to one embodiment, the contact layer does not cover more than 80% of said surface in order to enable an optimum absorption of the exudates by the compress.

The contact layer is advantageously configured so that it covers, before being exposed to the exudates of the wound, between 50% and 80%, preferably between 65% and 75%, of the surface of the compress that is opposite the wound.

The basis weight of the contact layer preferably ranges from 110 to 250 g/m2, more preferably from 160 to 200 g/m2. It is for example of the order of 185 g/m2.

The applicant therefore proposes a contact layer having a high basis weight and which covers a large proportion of the surface of the compress. Against all expectations, this contact layer does not hamper the compress's rate and capacity for absorbing exudates.

According to one embodiment, the contact layer has the form of a net fabric of yarns, the thickness of which—measured in the plane parallel to its greatest surface area—is between 1 and 3 mm, and the spacing of which is between 1 and 3 mm.

In one embodiment of the invention, the basis weight of the compress and the basis weight of the contact layer are substantially identical. The difference between the two basis weights is, for example, less than 20%, more preferably less than 10%, relative to the value of the highest basis weight.

The size, the shape and the relative arrangement of the openings of the contact layer are chosen so that said layer is sufficiently resistant to the deformations imposed during its application to the nonwoven compress, for example during a hot demolding step. The openings must also be large enough and the yarns of compositions must be thin enough so that the compress can absorb the exudates more rapidly than the hydrocolloids dispersed in the contact layer.

One particular embodiment of the invention is such that said layer:

is in the form of a net fabric of yarns, for which the thickness of the yarns—measured in the plane parallel to its greatest surface area—is between 1 and 3 mm, and for which the spacing between the yarns is between 1 and 3 mm, has a basis weight ranging from 170 to 200 g/m2, and comprises from 12% to 16% by weight of hydrocolloids relative to the weight of the composition that forms the contact layer.

The features which have been described above in connection with the present invention apply of course to this particular embodiment. For example, the basis weight of the compress may be substantially equal to that of the contact layer.

It will be preferred for the process of coating the compress with the contact layer to use a transfer step on an etched cylinder. The cylinder is soaked in the molten elastomer composition, before demolding the still-hot mesh on the nonwoven compress. This process advantageously makes it possible to incorporate solid hydrocolloid particles of relatively large particle size. The application of the still-hot composition to the compress additionally makes it possible to optimize the attachment of the contact layer on the compress. The invention is illustrated by the following example.

EXAMPLE 1

Preparation of the Nonwoven

A nonwoven of 185 g/m2 and having a thickness of 2 mm was prepared using LANSEAL® F superabsorbent fibers sold by the company Toyobo Co. Ltd., and polyester/polyethylene bicomponent thermal bonding fibers, in a 70% (superabsorbent fibers)/30% (thermal bonding fibers) weight ratio.

The fibers are weighed, mixed, carded, then napped in order to obtain a web of fibers. A needle-punching operation then makes it possible to consolidate this web. The final consolidation of the nonwoven takes place by heating (calendering) in order to melt the shell of the thermal bonding fibers and lock the nonwoven in its final configuration.

Preparation of the Hydrocolloid Elastomer Mass

A hydrocolloid elastomer composition was furthermore prepared by mixing in a mixer.

The elastomer composition, expressed as a weight percentage relative to the total weight of the composition, was the following:
  mineral oil sold by the company Shell under the name Ondina® 919: 41.7%;
  sodium salt of carboxymethyl cellulose (hydrocolloid) sold by the company AQUALON under the name CMC Blanose® 7H4XF: 14.8%;
  poly(styrene-ethylene-butylene-styrene) block copolymer sold by the company Kraton under the name KRATON® G 1651 E: 4.7%;
  antioxidant sold under the name IRGANOX® 1010 by the company Ciba Specialty Chemicals: 0.2%;
  tackifying resin sold by the company Exxon Chemicals under the name ESCOREZ® 5380: 35.6%;
  copolymer of a salt of 2-methyl-2[(1-oxo-2-propenyl)amino]-1-propanesulfonic acid and of the 2-hydroxyethylester of propenoic acid sold by SEPPIC under the name SEPINOV® EMT 10: 5%.

The various constituents were introduced at a temperature between 105° C. and 115° C. with stirring, so as to obtain a homogeneous mixture.

More specifically, initially the mineral oil, the hydrocolloid, and the elastomer then the antioxidant, the SEPINOV® EMT 10 and finally the tackifying resin were introduced.

Coating of the Nonwoven with the Adhesive Mass

This adhesive was coated onto the nonwoven at a basis weight of 180 g/m2 in the form of a net fabric, the mesh of which is square. The coating is carried out by hot-melt transfer on an etched cylinder. The width of the yarns is 1.6 mm. The square openings have a surface area of 4 mm2. The surface covered is 70%. The thickness of the yarns of the adhesive mass is 0.2 mm.

Test of the Removal of the Fibrin Matrix In Vitro

The fibrin matrices were prepared according to the Brown protocol described in the publication "Fibroblast migration in fibrin gel matrices" Arm J. Pathol, 1993, 142: 273-283.

The components and the procedure which were used are the following:
  Dissolved at 37° C. were:
  5 ml of an aqueous solution comprising 50 millimol of HEPES (Sigma-Aldrich catalogue);
  15 mg of fibrinogen from human plasma (Sigma-Aldrich catalogue);
  5 millimol of CaCl2.
  Added to the solution thus prepared were 50 µl of thrombin, 100 NIH, from human plasma (Sigma-Aldrich catalogue).

The assembly was deposited in a Petri dish then left to incubate at 37° C. for 24 hours.

At the end of 24 hours, the fibrin matrix is formed. A sample of dressing manufactured as above is deposited on the matrix, at ambient temperature, for 24 hours.

On removal, it is observed that the fibrin was detached from the support and transferred as a single block to the surface of the dressing that was removed.

COMPARATIVE EXAMPLES 2 AND 3

Preparation of the Nonwoven

The preparation of the nonwoven of the comparative examples 2 and 3 is identical to that described in example 1.

Composition of the Hydrocolloid Elastomer Mass of Comparative Example 2

The elastomer composition of comparative example 2 was identical to that described in example 1.

Composition of the Hydrocolloid Elastomer Mass of Comparative Example 3

The elastomer composition, expressed as a weight percentage relative to the total weight of the composition, was the following:
  mineral oil sold by the company Shell under the name Ondina® 917: 32.62%;
  sodium salt of carboxymethyl cellulose (hydrocolloid) sold by the company AQUALON under the name CMC Blanose® 7H4XF: 30%;
  poly(styrene-ethylene-butylene-styrene) block copolymer sold by the company Kraton under the name KRATON® G 1651 E: 3.86%;
  antioxidant sold under the name IRGANOX® 1010 by the company Ciba Specialty Chemicals: 0.16%;
  tackifying resin sold by the company Exxon Chemicals under the name ESCOREZ® 5380: 25%;
  copolymer of a salt of 2-methyl-2[(1-oxo-2-propenyl)amino]-1-propanesulfonic acid and of the 2-hydroxyethylester of propenoic acid sold by SEPPIC under the name SEPINOV® EMT 10: 11%.

Preparation of the Hydrocolloid Elastomer Mass of Comparative Examples 2 and 3

The preparation of the hydrocolloid elastomer mass of the comparative examples is identical to that described in example 1.

Coating of the Nonwoven with the Adhesive Mass

For comparative example 2, the adhesive was coated onto the nonwoven at a basis weight of 662 g/m2 in the form of a net fabric, the mesh of which is square. The coating was carried out by hot-melt transfer on an etched cylinder. The thickness of the yarns was 0.84 mm.

For comparative example 3, the adhesive was coated onto the nonwoven at a basis weight of 840 g/m2 in the form of a net fabric, the mesh of which is square. The coating was carried out by hot-melt transfer on an etched cylinder. The thickness of the yarns was 1 mm.

Measurement of the Absorption Capacity

The measurement of the absorption capacity was carried out according to the standard EN ISO 9073-12 relative to the measurement of the absorption capacity of a nonwoven, apart from the difference that a porous glass sheet having a diameter of 30 mm was used and that the hydrophobic foam piece/weight assembly was replaced by a Plexiglas sheet/weight which applies overall a pressure of 40 mm of mercury.

The liquid used was a solution of NaCl/CaCl2 which comprised 298 g of NaCl and 368 g of CaCl2 per liter of water.

The absorption results expressed in grams have been reported in the table below.

| Products | Mass of NaCl/CaCl2 solution absorbed at the end of 1 h (g) | Mass of NaCl/CaCl2 solution absorbed at the end of 24 h (g) |
|---|---|---|
| Example 1 | 3.016 | 11.976 |
| Comparative example 2 | 0.459 | 8.847 |
| Comparative example 3 | 0.364 | 8.348 |

The dressing of comparative example 2, for which the basis weight of the hydrocolloid elastomer mass is greater than 500 g/m$^2$, absorbs—at 1 hour and at 24 hours—much less than the dressing of example 1 of the invention even though the content of hydrocolloids is identical.

The dressing of comparative example 3, for which the basis weight of the hydrocolloid elastomer mass is greater than 500 g/m$^2$ and for which the amount of hydrocolloid is greater than 20% by weight, absorbs—at 24 hours—less than the dressing of example 1 of the invention. The use of the specific contact layer of example 1 demonstrates that the absorption rate of the nonwoven is not slowed down and that this absorption capacity is retained over time unlike the contact layers defined in the counterexamples.

The invention claimed is:

1. A dressing for healing an exudating wound, comprising:
    an exudate superabsorbent nonwoven compress; and
    a micro-adherent wound contact layer attached to a face of the exudate superabsorbent nonwoven compress without a fabric substrate and configured to come into contact with an exudating wound and avoid contact of the exudate superabsorbent nonwoven compress with the exudating wound,
    the exudate superabsorbent nonwoven compress being formed from a mixture of bicomponent superabsorbent fibers and of thermal bonding non-absorbent fibers, all of the fibers being thermally bonded, wherein
    the wound contact layer does not adhere to the exudating wound, the wound contact layer comprising openings that allow the passage of exudates from the exudating wound and having a basis weight that ranges from 110 to 500 g/m$^2$,
    the wound contact layer is a micro-adherent elastomer composition comprising an elastomeric matrix and hydrocolloids, the proportion of hydrocolloids being between 2% and 20% by weight of the weight of said wound contact layer,
    the micro adherent elastomer composition comprises:
    0.05% to 1% by weight of antioxidant;
    30% to 40% by weight of tackifying resin;
    2% to 20%, by weight of hydrocolloid;
    35% to 45% by weight of plasticizer;
    4% to 6% by weight of a poly(styrene-ethylene-butylene-styrene) or poly(styrene-ethylene-propylene-styrene) triblock polymer; and
    2% to 8% by weight of a copolymer consisting of a salt of 2 methyl-2 [(1 oxo-2 propenyl)amino]-1 propane-sulfonic acid and of the 2 hydroxyethylester of propenoic acid, and
    the wound contact layer gels in contact with wound exudates without reduction of a size of the wound contact layer openings, and creates a moist environment on the exudating wound.

2. The dressing as claimed in claim 1, wherein the thermal bonding non-absorbent fibers are bicomponent fibers.

3. The dressing as claimed in claim 2, wherein the thermal bonding non-absorbent fibers are bicomponent fibers of core/shell type, said core being made of polyethylene terephthalate and the shell being made of polyethylene.

4. The dressing as claimed in claim 1, wherein the bicomponent superabsorbent fibers are bicomponent fibers of core-shell type, said core being made of polyacrylonitrile and the shell being made of polyacrylate.

5. The dressing as claimed in claim 1, wherein the basis weight of the compress ranges from 40 to 400 g/m$^2$.

6. The dressing as claimed in claim 1, wherein the thickness of the compress ranges from 0.6 to 3 mm.

7. The dressing as claimed in claim 1, wherein the weight ratio between the bicomponent superabsorbent fibers and the thermal bonding non-absorbent fibers is between 60/40 and 80/20.

8. The dressing as claimed in claim 1, wherein the basis weight of the contact layer ranges from 150 to 200 g/m$^2$.

9. The dressing as claimed in claim 1, wherein the contact layer, before being exposed to the exudates of the wound, covers between 50% and 80%, of the face of the compress that in use faces the wound.

10. The dressing as claimed in claim 1, wherein the contact layer is in a form of a net fabric of yarns and has a thickness, measured in the plane parallel to its greatest surface area, of between 1 and 3 mm, and the spacing of the yarns is between 1 and 3 mm.

11. The dressing as claimed in claim 1, wherein each of the openings of the contact layer has a surface area between 0.5 and 10 mm$^2$.

12. The dressing as claimed in claim 1, wherein the hydrocolloids are chosen from alkali metal salts of carboxymethyl cellulose.

13. The dressing as claimed in claim 1, wherein the hydrocolloids represent from 8% to 18% by weight relative to the total weight of the composition.

14. The dressing as claimed in claim 1, wherein the hydrocolloids represent from 12% to 16% by weight relative to the total weight of the composition.

15. The dressing as in claim 1, wherein the dressing absorbs fluid exudates and viscous exudates that are produced by the exudating wound.

16. The dressing as in claim 1, wherein the openings are square openings.

17. An absorbent dressing for healing an exudating wound, comprising:
- a—an exudate superabsorbent nonwoven compress formed from a mixture of bicomponent superabsorbent fibers and of thermal bonding non-absorbent fibers, all of the fibers being thermally bonded, and,
- b—a micro-adherent wound contact layer attached to a face of the superabsorbent nonwoven compress that in use faces the exudating wound and avoids contact of the superabsorbent nonwoven compress with the exudating wound, said wound contact layer comprising openings which cover between 50% and 80% of the face of the exudate superabsorbent nonwoven compress before being exposed to exudates from the exudating wound, so that said openings allow passage of the exudates from the exudating wound during healing of the exudating wound, and each of the openings of the wound contact layer has a surface area between 0.5 and 10 $mm^2$, the micro-adherent wound contact layer comprising an micro adherent elastomer composition that comprises:
0.05% to 1% by weight of antioxidant;
30% to 40% by weight of tackifying resin;
2% to 20%, by weight of hydrocolloid;
35% to 45% by weight of plasticizer comprising mineral oil;
4% to 6% by weight of a poly(styrene-ethylene-butylene-styrene) or poly(styrene-ethylene-propylene-styrene) triblock polymer; and
2% to 8% by weight of a copolymer consisting of a salt of 2 methyl-2 [(1 oxo-2 propenyl)amino]-1 propanesulfonic acid and of the 2 hydroxyethylester of propenoic acid, and the wound contact layer having a basis weight that ranges from 110 to 500 $g/m^2$, and said wound contact layer is an elastomeric matrix in which hydrocolloids are homogeneously dispersed, the proportion of hydrocolloids being between 2% and 20% by weight of the weight of said wound contact layer, and the wound contact layer being attached to the exudate superabsorbent nonwoven compress without a fabric substrate, in order that the absorbent dressing remains flexible and adopts the shape of a body.

18. The absorbent dressing as in claim 17, wherein the dressing absorbs fluid exudates and viscous exudates that are produced by the exudating wound.

19. The absorbent dressing as in claim 17, wherein the thermal bonding non-absorbent fibers are bicomponent fibers.

20. The absorbent dressing as in claim 19, wherein the thermal bonding non-absorbent fibers are bicomponent fibers of core/shell type, said core being made of polyethylene terephthalate and the shell being made of polyethylene.

21. The absorbent dressing as in claim 17, wherein the bicomponent superabsorbent fibers are bicomponent fibers of core-shell type, said core being made of polyacrylonitrile and the shell being made of polyacrylate.

22. The absorbent dressing as in claim 17, wherein the basis weight of the compress ranges from 40 to 400 $g/m^2$.

23. The absorbent dressing as in claim 17, wherein the thickness of the compress ranges from 0.6 to 3 mm.

24. The absorbent dressing as in claim 17, wherein the weight ratio between the bicomponent superabsorbent fibers and the thermal bonding non-absorbent fibers is between 60/40 and 80/20.

25. The absorbent dressing as in claim 17, wherein the basis weight of the contact layer ranges from 150 to 200 $g/m^2$.

26. The absorbent dressing as in claim 17, wherein the contact layer is in a form of a net fabric of yarns and has a thickness, measured in the plane parallel to its greatest surface area, of between 1 and 3 mm, and the spacing of the yarns is between 1 and 3 mm.

27. The absorbent dressing as in claim 17, wherein the hydrocolloids are chosen from alkali metal salts of carboxymethyl cellulose.

28. The absorbent dressing as in claim 17, wherein the hydrocolloids represent from 8% to 18% by weight relative to the total weight of the composition.

29. The absorbent dressing as in claim 17, wherein the hydrocolloids represent from 12% to 16% by weight relative to the total weight of the composition.

30. The absorbent dressing as in claim 17, wherein the openings are square openings.

* * * * *